(12) United States Patent
Vertesy et al.

(10) Patent No.: US 6,927,236 B2
(45) Date of Patent: Aug. 9, 2005

(54) CONIOSULFIDES AND THEIR DERIVATIVES, PROCESSES FOR PREPARING THEM, AND THEIR USE AS PHARMACEUTICALS

(75) Inventors: Laszlo Vertesy, Eppstein-Vockenhausen (DE); Klaus Ehrlich, Russelsheim (DE); Michael Kurz, Hochheim (DE); Marian Paul Segeth, Idstein (DE); Luigi Toti, Hochheim (DE)

(73) Assignee: Aventis Pharma Deutschland GmbH., Frankfurt (DE)

( * ) Notice: Subject to any disclaimer, the term of this patent is extended or adjusted under 35 U.S.C. 154(b) by 0 days.

(21) Appl. No.: 10/247,102

(22) Filed: Sep. 19, 2002

(65) Prior Publication Data

US 2003/0158117 A1 Aug. 21, 2003

Related U.S. Application Data

(60) Provisional application No. 60/358,466, filed on Feb. 20, 2002.

(30) Foreign Application Priority Data

Sep. 22, 2001 (DE) ......................................... 101 46 737

(51) Int. Cl.[7] ........................ A01N 37/00; A01N 37/12; A01N 37/44; A61K 31/20; A61K 31/195
(52) U.S. Cl. ...................... 514/549; 514/560; 514/562; 514/563; 560/150; 560/153; 562/557
(58) Field of Search ................................ 514/549, 560, 514/562, 563; 560/150, 153; 562/557

(56) References Cited

FOREIGN PATENT DOCUMENTS

WO    WO 98/21327    5/1998

OTHER PUBLICATIONS

Lue et al, "Soluble Amyloid beta Peptide Concentration as a Predictor of Synaptic Change in Alzheimer's Disease" American Journal of Pathology, vol. 155(3), pp. 853–862 (1999).*
Mclean et al, "Soluble Pool of A–beta Amyloid as a Determinant of Severity of Neurodegeneration in Alzheimer's Disease" Annals of Neurology, vol. 46(6), pp. 860–866 (Dec. 1999).*
Reichman, W.E., "Alzheimer's Disease: Clinical Treatment Options" vol. 6(22) Sup., pp. S1125–S1138 (Dec. 2000).*
Sabo et al, "The Alzheimer Amyloid Precursor Protein (APP) and FE65, an APP–binding Protein, Regulate Cell Movement" The Journal of Cell Biology, vol. 153, pp. 1403–1414 (2001).*
Klein, W., "A.beta. toxicity in Alzheimer's disease: globular oligomers (ADDLs) as new vaccine and drug targets" Neurochemist International, vol. 41, pp. 345–352 (2002).*
Bryant A. Gilbert et al., Structure– Activity Studies on the Retinal Rod Outer Segment Isoprenylated Protein Methytransferase, J. Am. Chem. Soc. (1992, pp. 3966–3973, vol. 114).
Dennis Selkoe, The Cell Biology of b–amyloid precursor protein and presenilin in Alzheimer's Disease, Trends in Cell Biology (1998, pp. 447–453, vol. 8).
Eng Wui Tan et al., Heteroatom Requirements for Substrate Recognition by GTP–Binding Protein Methyltransferase, J. Am. Chem. Soc. (1991, pp. 6299–6300, vol. 113).
Glomset, J.A., Prenyl proteins in eukaryotic cells: a new type of membrane anchor, Trends in Biochemical Sciences (1990, pp. 139–142, vol. 15).
Tokichi Miyakawa et al., Role of Metabolism of the Mating Pheromone in Sexual Differentiation of the Heterobasidiomycete Rhodosporidium, Journal of Bacteriology, (1982, pp. 1184–1194, vol. 151, No. 3).
Alterserkrankungen "Alzheimer" und "Parkinson", PdN–Bio (1999, pp. 26–31, vol. 6, No. 48).

* cited by examiner

Primary Examiner—James O. Wilson
Assistant Examiner—Zachary C. Tucker
(74) Attorney, Agent, or Firm—Irving Newman

(57) ABSTRACT

The present invention relates to compounds of the formula

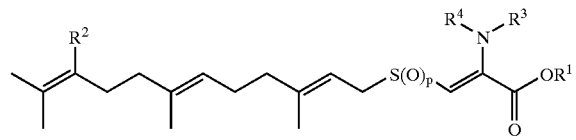

(I)

which are formed during fermentation by the microorganism *Coniochaeta ellipsoidea* Udagawa, DSM 13856, or by one of its mutations and/or variants, and chemically derivatized if appropriate. The invention furthermore relates to a process for preparing compounds of the formula (I), and to their use as pharmaceuticals. In addition, the invention relates to the use of a compound of the formula (VI)

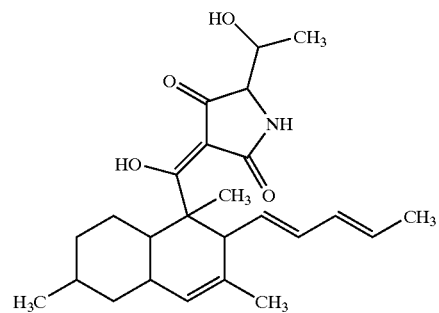

(VI)

for producing a pharmaceutical for the treatment and prophylaxis of degenerative neuropathics or of Alzheimer's disease.

16 Claims, No Drawings

CONIOSULFIDES AND THEIR DERIVATIVES, PROCESSES FOR PREPARING THEM, AND THEIR USE AS PHARMACEUTICALS

RELATED APPLICATIONS

This application claims the benefit of U.S. Provisional Application No. 60/358,466 filed Feb. 20, 2002, which is hereby incorporated by reference in its entirety.

DESCRIPTION OF THE INVENTION

Coniosulfides and their derivatives, processes for preparing them, and their use as pharmaceuticals.

According to the current state of knowledge, Alzheimer's disease (dementia of the Alzheimer type, AD) is a hereditary, inexorably progressing atrophy of the cerebral cortex which is associated with increasing mental disturbance. Alzheimer's disease is a neuropsychiatric disease which mainly occurs in the elderly. The disease manifests itself in a complex of symptoms which include memory disturbances, diminished power of observation, orientation disturbances, speech disturbances, disturbances in the ability to think logically, etc. Characteristic neurohistological changes are found in Alzheimer's patients, such as the deposition of what are termed amyloid plaques and degeneration of the neurofibrils in the nerve cells (what are termed "fibrillary bundles"). While these changes are characteristic, they are in no way specific since they also occur to a lesser degree in association with the normal ageing process.

At present, it is only possible to treat AD symptomatically and not causally. The drugs which have thus far become available are only able to delay the course of the disease and cannot cure it. The most important therapeutic approach is offered by the cerebral acetylcholine esterase inhibitor group (Tacrin®, Donepezil®, Rivastigmin®, Galantamin®), since cholinergic signal transmission is of great important for the memory-relevant structures which are impaired to a particularly high degree in AD. However, the drugs can only be employed when the disease is at the mild and moderate stages. The drugs increase the concentration of acetylcholine in the information-transmitting synapses in the brain. They are no longer effective when the damage to the neurons is too great, that is in the late stage of the disease. Other substances whose use is being tested are estrogens, non-steroidal analgesics, antioxidants and nerve growth factors (NGFs). However, none of these agents is sufficiently effective for treating Alzheimer's disease.

It is estimated that, at the present time, about a million people in the Federal Republic of Germany are suffering from Alzheimer's disease. This number will presumably increase still further in the next two years due to rising life expectation within the population (F. Kohl, Prax. Naturwiss. Biol. (1999), 48(6), 26–31). There is therefore a pressing need for novel substances for treating this disease.

What are termed the amyloid plaques represent the histological changes in the brain which are characteristic of AD. These plaques are pathological depositions of the β-amyloid peptide, or the βA4-protein, which, as a result of a metabolic defect, is split off from a physiological cell membrane constituent, i.e. the amyloid precursor protein (APP). It then becomes concentrated within the brain, where it can no longer be degraded by the body and appears as a plaque (F. Kohl, Prax. Naturwiss. Biol. (1999), 48(6), 26–31; D. J. Selkoe; Trends Cell Biol. (1998), 8, 447–453). The essential element of the amyloid plaque is a peptide comprising 39 to 43 amino acids, i.e. what is termed β-amyloid or Aβ. This peptide is formed during the processing of the APP. Mutations in the genes which encode this processing have been found in patients who are suffering from the hereditary form of AD. An increase in the production of Aβ was observed in the same patients, from which it was considered that the processing of the APP could possibly be a suitable point of attack for treating Alzheimer's disease. The constituent tetrapeptide sequence Asn-Pro-Thr-Tyr plays a role in the processing of the APP. This constituent sequence is recognized by the proteins COFE65 and, in particular, FE65, and it is assumed that these proteins are involved in the protein-protein interaction which is responsible for the APP processing (WO 98/21327). Agents which inhibit the APP-FE65 interaction should therefore be valuable remedies for treating AD.

The present invention relates to novel active compounds (coniosulfides) of the farnesyl thiopeptide type which are formed during fermentation by the microorganism *Coniochaeta ellipsoidea* Udagawa, DSM 13856, to chemical derivatives of the coniosulfides, to a process for preparing them, and to the use of coniosulfides and their derivatives as pharmaceuticals.

Some compounds having a farnesyl thiopeptide basic structure have already been described. T. Miyakawa et al. (Journal of Bacteriology (1982), 151, 1184–1194) isolated a farnesyl undecapeptide, which is a pheromone which is of importance for the pairing of the organism, from cultures of *Rhodosporidium toruloides*.

Eng Wui Tan et al. (J. Am. Chem. Soc. (1991), 113, 6299–6300); J. Am. Chem. Soc. (1992), 114, 3966–3973) synthesized farnesylcysteine and farnesylcysteine oxide,

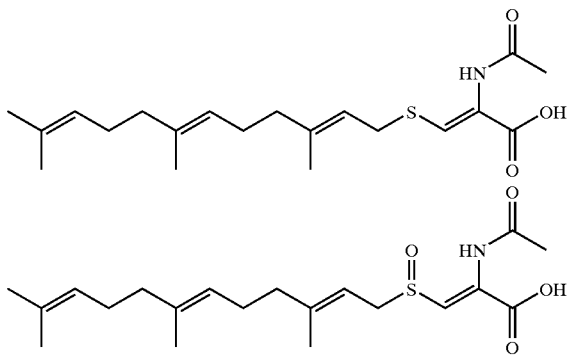

which are good substrates of isoprenylated protein methyltransferase.

The importance of the prenylation of proteins for their anchoring into biological membranes has already previously been disclosed (J. A. Glomset et al., Trends in Biochem. Sciences (1990), 15,139–142).

Miyakawa et al. (J. Bacteriol. (1982), 151, 1184–1194) describe the compounds rhodotorucine A (p=0) and rhodotorucine-A-S-oxide (p=1),

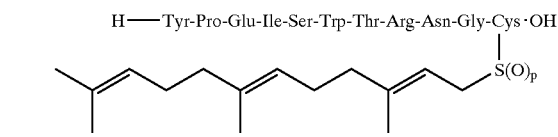

as being sexual hormones of the *Rhodosporidium toruloides* type A cell.

It has been found, surprisingly, that the strain *Coniochaeta ellipsoidea* Udagawa, DSM 13856, is able to form novel compounds which not only effectively inhibit the APP-FE65 interaction but are also well tolerated. These compounds are the farnesyl thiopeptide derivatives of the formula (I), which are termed coniosulfides and which are described below.

The invention relates to a compound of formula (I)

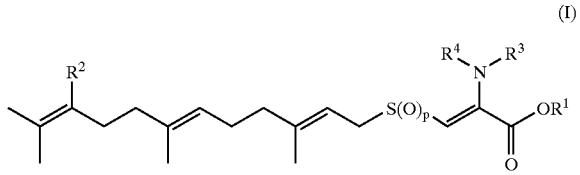

(I)

where
$R^1$ is
 1.0 H, or
 2.0 a radical selected from —$C_1$–$C_6$-alkyl, —$C_2$–$C_6$-alkenyl, —$C_2$–$C_6$-alkynyl or —$C_6$–$C_{10}$-aryl, which can be substituted once or twice by
  2.1 —OH,
  2.2 =O,
  2.3 —O—$C_1$–$C_6$-alkyl,
  2.4 —O—$C_2$–$C_6$-alkenyl,
  2.5 —$C_6$–$C_{10}$-aryl,
  2.6 —NH—$C_1$–$C_6$-alkyl,
  2.7 —NH—$C_2$–$C_6$-alkenyl,
  2.8 —$NH_2$ or
  2.9 fluorine, chlorine, bromine or iodine,
  in which the substituents 2.3 to 2.8 can also be still further substituted by —CN or -amide functions,
 3.0 —($C_1$–$C_4$-alkyl)-($C_6$–$C_{10}$-aryl), or
 4.0 —$NH_2$, —NH—($C_1$–$C_6$-alkyl), —NH—($C_2$–$C_6$-alkenyl),
$R^2$ H, methyl, ethyl, n-propyl, isopropyl, n-butyl or isobutyl,
$R^3$ is a radical which is composed of from 1 to 10 amino acids and which can be N-terminally protected with a —CO—($C_1$–$C_6$-alkyl) group or a —$C_1$–$C_6$-alkyl group,
$R^4$ H, —$C_1$–$C_6$-alkyl, —CO—($C_1$–$C_6$-alkyl), —CO—($C_2$–$C_6$-alkenyl) or —($C_1$–$C_4$-alkyl)-($C_6$–$C_{10}$-aryl), and
p is an integer 0, 1 or 2,
with the exception of the compounds of formula (I) in which, all at the same time,
$R^1$ is H,
$R^2$ is H,
$R^3$ is —CO—$CH_3$,
$R^4$ is H, and
p is 0 or 1,
and/or a stereoisomeric form of the compound of the formula (I), and/or mixtures of these forms in any ratio,
and/or complexes or adducts of the compound of the formula (I),
and/or a physiologically tolerated salt of the compound of the formula (I).
$R^1$ is preferably H.
$R^2$ is preferably H or methyl, particularly preferably methyl.
$R^3$ is preferably a radical which is composed of from 1 to 2 amino acids, preferably natural amino acids, particularly preferably uncharged natural amino acids, and which can be N-terminally protected, preferably with an acetyl group.
$R^4$ is preferably H,
p is preferably 0.

The invention preferably relates to a compound of the formula (I) in which $R^4$ is H and $R^1$, $R^2$, $R^3$ and p are defined as above.

The invention furthermore preferably relates to a compound of formula (I) in which $R^4$ is hydrogen, and p is zero and $R^1$, $R^2$ and $R^3$ are defined as above.

Particularly preferably, the invention relates to a compound of the formula (I) in which $R^2$ is H or methyl, $R^4$ is hydrogen and p is zero and $R^1$ and $R^3$ are defined as above.

The invention furthermore particularly preferably relates to a compound of the formula (I) in which $R^2$ is H or methyl, $R^3$ is a radical which is composed of from 1 to 2 amino acids and which can be N-terminally protected, $R^4$ is hydrogen and p is zero and $R^1$ is defined as above.

Especially preferably, the invention relates to a compound of the formula (I) in which $R^1$ is H, $R^2$ is H or methyl, $R^3$ is a radical which is composed of from 1 to 2 amino acids and which can be N-terminally protected, $R^4$ is hydrogen and p is zero.

Particularly especially preferably, the invention relates to a compound of the formula (I) in which $R^1$ is hydrogen, $R^2$ is hydrogen or methyl, $R^3$ is a Gly or Gly-Gly radical, which can be N-terminally protected, $R^4$ is hydrogen and p is zero.

Amino acids can have the D configuration or the L configuration. Natural amino acids are the encodable amino acids and have the L configuration. Natural neutral amino acids are glycine (Gly), L-alanine (Ala), L-valine (Val), L-leucine (Leu), L-isoleucine (Ile), L-proline (Pro), L-tryptophan (Typ), L-penylalanine(Phe) and L-methionine (Met).

$C_1$–$C_6$-alkyl is a straight-chain or branched alkyl group having from 1 to 6 C atoms, preferably having from 1 to 4 C atoms, for example methyl, ethyl, n-propyl, i-propyl, n-butyl, tert-butyl or n-hexyl.

$C_2$–$C_6$-alkenyl is a straight-chain or branched alkenyl group which has from 2 to 6 C atoms and which is unsaturated once, twice or three times, such as allyl, crotyl, 1-propenyl, penta-1,3-dienyl or pentenyl.

$C_2$–$C_6$-alkynyl is a straight-chain or branched alkynyl group which has from 2 to 6 C atoms and which contains one or two triple bonds, for example propynyl, butynyl or pentynyl.

$C_6$–$C_{10}$-aryl is an aryl group which has from 6 to 10 ring C atoms, for example phenyl or naphthyl and which can be substituted, once or more than once, by, for example, chlorine, bromine, fluorine, iodine, —$C_1$–$C_4$-alkyl, preferably methyl, hydroxyl, —O—($C_1$–$C_4$-alkyl), preferably methoxy, or by perfluorinated $C_1$–$C_4$-alkyl radicals, preferably trifluoromethyl.

—($C_1$–$C_4$-Alkyl)-($C_6$–$C_{10}$-aryl) is preferably benzyl.

—CO—($C_1$–$C_6$-alkyl) is an aliphatic acyl group having from 2 to 7 C atoms, preferably from 2 to 5 C atoms, for example formyl, acetyl, propionyl, butyryl, hexanoyl, acryloyl, crotonoyl, propioloyl, which group can be still further substituted, for example by chlorine, bromine, fluorine, iodine, $NH_2$, or —($C_1$–$C_4$-alkyl)-$NH_2$, preferably methylamino or ethylamino.

—CO—($C_2$–$C_6$-Alkenyl) is an aliphatic acyl group having from 3 to 7 C atoms, preferably from 3 to 5 C atoms, for example acryloyl, crotonoyl or propioloyl, which group can be still further substituted, for example by chlorine, bromine, fluorine, iodine, $NH_2$ or —($C_1$–$C_4$-alkyl)-$NH_2$, preferably methylamino or ethylamino.

—CO—($C_6$–$C_{10}$-Aryl) is an aromatic acyl group having from 6 to 10 ring C atoms, for example benzoyl or naphthoyl, which can also be still further substituted, for example by chlorine, bromine, fluorine, iodine, $C_1$–$C_4$-alkyl, preferably methyl, hydroxyl, —($C_1$–$C_4$-alkyl)-$NH_2$, preferably methylamino or ethylamino, —O—($C_1$–$C_7$-alkyl), preferably —O—($C_1$–$C_4$-alkyl), in particular methoxy.

If not otherwise indicated, chiral centers in the compounds of the formula (I) can, independently of each other, be present in the R configuration or the S configuration. Double bonds can, independently of each other, be present in the cis position or in the trans position. The invention relates both to the optically pure compounds and to stereoisomeric mixtures, such as enantiomeric mixtures and diastereomeric mixtures, in any ratio.

The invention preferably relates to a compound of the formula (II)

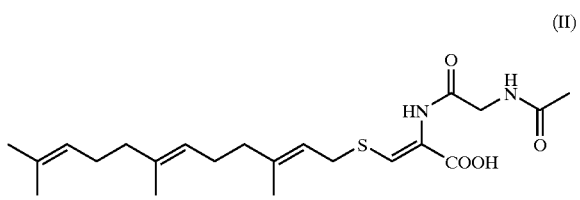

(II)

(Coniosulfide A: empirical formula: $C_{22}H_{34}O_4N_2S$, MW. 422.59), to a compound of the formula (III)

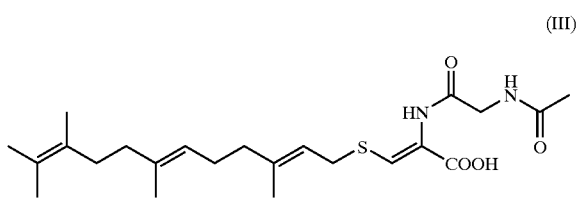

(III)

(Coniosulfide B, $C_{23}H_{36}N_2O_4S$, MW. 436.62), to a compound of the formula (IV)

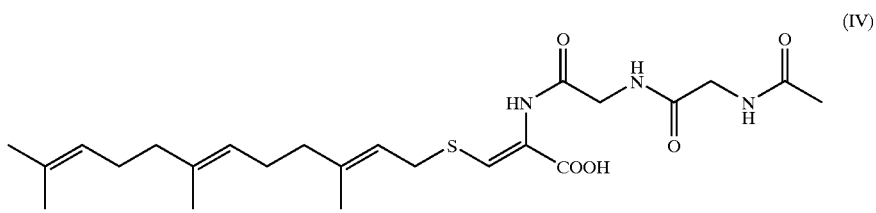

(IV)

(Coniosulfide C, $C_{24}H_{37}N_3O_5S$, MW. 479.64) and to a compound of the formula (V)

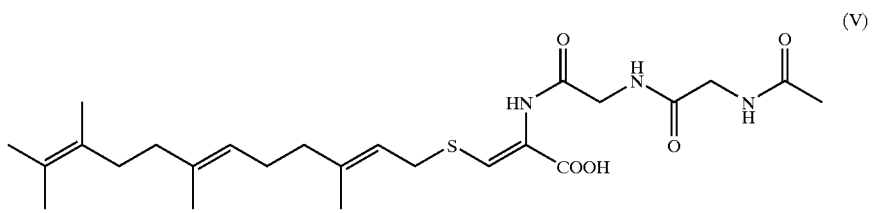

(V)

(Coniosulfide D, $C_{25}H_{39}O_5N_3S$, MW. 493.67), and to their obvious chemical equivalents and/or physiologically tolerated salts.

Obvious chemical equivalents of the compounds of the formulae (I) to (V) are compounds which exhibit a trivial chemical difference and which consequently have the same activity or are converted, under mild conditions, into the compounds according to the invention. Said equivalents include, for example, esters, azomethines (Schiff's bases), hydrogenation products, reduction products, complexes or addition compounds of or with the compounds according to the invention, all of which are prepared using methods known in the literature (J. March, Advanced Organic Synthesis, 4$^{th}$ Edition, John Wiley & Sons, 1992).

Double bonds in the alkyl chain in compounds of the formula (I) can be reduced, for example, by means of hydrogenolysis or using other methods which are known per se, for example as described by P. N. Rylander in "Hydrogenation Methods", Academic Press, New York (1985), Chapter 2, or by H. O. House in "Modern Synthetic Reactions", W. A. Benjymin, Inc., New York (1972), pages 446–452. In addition, the double bonds can be oxidized to epoxides, for example using meta-chloroperbenzoic acid (MCPBA; J. March, Advanced Organic Synthesis, 4$^{th}$ Edition, John Wiley & Sons, 1992).

The compounds of the formulae (I) to (V) according to the invention, and also the obvious chemical equivalents of these compounds, can be converted into the corresponding physiologically tolerated salts using methods which are known to the skilled person.

Physiologically tolerated salts of the compounds according to the invention are understood as being both inorganic and organic salts, as are described in Remingtons Pharmaceutical Sciences (17th edition, page 1418 [1985]). Particularly suitable salts are alkali metal salts, ammonium salts, alkaline earth metal salts, salts with physiologically tolerated amines and salts with inorganic or organic acids, such as HCl, HBr, $H_2SO_4$, maleic acid and fumaric acid.

The compounds of the formula (I) according to the invention differ from substances known from the literature. While structurally related farnesyl thiopeptides have been described (see above), they differ from the compounds according to the invention in their precise chemical structure and in their activity.

The invention additionally relates to a compound of the formula (I) which can be obtained by fermenting Coniochaeta ellipsoidea Udagawa, DSM 13856, or one of its mutants or variants, in a culture medium until a compound of the formula (I) accumulates in the culture medium, and then isolating the compound of the formula (I) and optionally derivatizing it and/or, where appropriate, converting it into a physiologically tolerated salt.

The invention furthermore relates to a process for preparing a compound of the formula (I), which comprises fermenting the microorganism Coniochaeta ellipsoidea Udagawa, DSM 13856, or a variant or mutant of *Coniochaeta ellipsoidea* Udagawa, DSM 13856, in a culture medium until a compound of the formula (I) accumulates in the culture broth, isolating the compound of the formula (I) and then optionally derivatizing it and, where appropriate, converting it into a pharmacologically tolerated salt.

When the compound of formula (I) is derivatized, methods which are known per se (J. March, Advanced Organic Chemistry, Wiley & Sons, $4^{th}$ ed. 1992) are used, for example, to alkylate or acylate the —$NR^3R^4$ group, in which $R^4$ is hydrogen, to oxidize the S atom of the sulfide group (p=0), for example using MCPBA, hydrogen peroxide or peracetic acid, or using other peracids, to a sulfoxide derivative (p=1) or sulfone derivative (p=2), and/or to esterify a free acid group in the compound of formula (I), in which $R^1$ is hydrogen, with an activated alcohol. The examples of activated alcohols are diazomethane or other alcohol derivatives.

In order to carry out reactions selectively, it can be advantageous to introduce suitable protecting groups, in a manner known per se, prior to the reaction. The protecting groups can be eliminated after the reaction, and the reaction product is subsequently purified, where appropriate.

The fungus *Coniochaeta ellipsoidea* Udagawa was deposited in the Deutsche Sammlung von Mikroorganismen und Zellkulturen [German Collection of Microorganisms and Cell Cultures] GmbH (DSM), Mascheroder Weg 1B, 38124 Brunswick, Germany, in accordance with the rules of Budapest Treaty, on Nov. 17, 2000 under the following number: DSM 13856. The fungus has a white substrate mycelium and very little aerial mycelium and, in culture, does not form any fruiting bodies which are characteirstic of *Coniochaeta*.

The process for preparing compounds of the formula (I) preferably comprises culturing *Coniochaeta ellipsoidea* Udagawa, DSM 13856, or its mutants and/or variants, under aerobic conditions in a culture medium which contains in each case one or more carbon sources, nitrogen sources, inorganic salts and, where appropriate trace elements.

Instead of the strain DSM 13856, it is also possible to use its mutants and/or variants provided they synthesize the compounds according to the invention.

Mutants are organisms which belong to the same species but which differ in their genes and which consequently constitute different genotypes ("genotype: The genetic constitution of an organism, usually in respect to one gene or a few genes relevant in a particular context", McGraw-Hill, Dictionary of scientific and technical terms, McGraw-Hill Book Company, New York 1978, page 672).

The preparation of mutants is described, inter alia, in Brock et al. "Biology of Microorganisms", Prentice Hall, pp. 238–247 (1994), according to which, for example, physical means, for example irradiation with ultraviolet rays or X-rays, or chemical mutagens, for example ethyl methanesulfonate (EMS); 2-hydroxy-4-methoxy-benzophenone (MOB) or N-methyl-N'-nitro-N-nitrosoguanidine (MNNG), can induce mutation.

While variants within the meaning of the invention have an identical genome, they differ in their wild-type phenotype ("Phenotype: The observable characters of an organism", McGraw-Hill, Dictionary of scientific and technical terms, McGraw-Hill Book Company, N. Y. 1978, page 1199). Microorganisms possess the ability to develop different phenotypes depending on their environment: "Microorganisms have the ability to adapt to environmental changes. This adaptive capacity is the reason for the observed physiological flexibility. In phenotypic adaptation, all cells of a population are involved. This type of change is not genetically conditioned. It is a modification that under altered conditions is reversible" (H. Stolp, "Microbial ecology: organisms, habitats, activities", Cambridge University Press, Cambridge, GB, 1988, page 180).

It is possible to screen for mutants and variants which are used in compounds according to the invention by determining the biological activity of the active compound which has accumulated in the culture broth or by means of high performance liquid chromatography (HPLC determination).

Examples of suitable carbon sources for the fermentation are assimilable carbohydrates and sugar alcohols, such as glucose, lactose, sucrose or D-mannitol, and also carbohydrate-containing natural products, such as malt extract or yeast extract. Examples of suitable nitrogen-containing nutrients are amino acids, peptides and proteins and also their breakdown products, such as caseine, peptones or tryptones, and, in addition, meat extracts, yeast extracts, ground seeds, for example derived from corn, wheat, beans, soya or the cotton plant, distillation residues from alcohol production, meat meals or yeast extract, and also ammonium salts and nitrates, in particular, however, peptides which are obtained synthetically or biosynthetically as well. The examples of inorganic salts which can be present in the nutrient solution are chlorides, carbonates, sulfates or phosphates of the alkali metals or alkaline earth metals, while examples of trace elements are iron, zinc, cobalt, molybdenum, boron, vanadium and manganese.

The culture medium preferably contains malt extract, yeast extract, glucose, starch, rolled oats and/or glycerol, particularly preferably in constituent amounts of from 0.05 to 5%, preferably from 1 to 2%, of malt extract, from 0.05 to 3%, preferably from 0.05 to 1%, of yeast extract, from 0.2 to 5%, preferably from 0.5 to 2%, of glucose and from 0.5 to 3%, preferably from 1.5 to 3%, of rolled oats, in each case based on the weight of the total nutrient solution.

In this nutrient solution, *Coniochaeta ellipsoidea* Udagawa, DSM 13856, forms a mixture of the compounds of the formula (I) according to the invention. The quantitative proportion of one or more of the coniosulfides according to the invention can vary depending on the composition of the nutrient solution. In addition, the composition of the medium can be used to control the synthesis of individual coniosulfides such that the microorganism does not produce a particular coniodisulfide at all or only produces it in a quantity which is below the limit of detection.

The microorganism is preferably cultured aerobically, that is, for example, submerged while being shaken or stirred in shaking flasks or fermenters, or on solid medium, where appropriate while introducing air or oxygen. The culture can be carried out in a temperature range of from about 15 to 35° C., preferably at from about 20 to 35° C., in particular at from 25 to 30° C. The pH range should be between 3 and 10, preferably between 6.5 and 7.5. The microorganism is generally cultured under these conditions over a period of from 48 to 960 hours, preferably of from 72 to 720 hours. Advantageously, it is cultured in several steps, i.e. one or more precultures are first of all prepared in a liquid nutrient medium, which precultures are then inoculated over into the actual production medium, i.e. the main culture, for example in a volume ratio of 1:10–1:100. The preculture is obtained, for example, by inoculating the mycelium into a nutrient solution and allowing it to grow for from about 20 to 120 hours, preferably for from 48 to 72 hours. The mycelium can be obtained, for example, by allowing the strain to grow for from about 1 to 40 days, preferably for from 21 to 35 days, on a solid or liquid nutrient medium, for example yeast-malt agar, rolled oats agar or potato dextrose agar.

The course of the fermentation, and the formation of the compounds according to the invention, can be monitored in accordance with methods known to the skilled person, for example by testing the biological activity in bioassays or by means of chromatographic methods such as thin layer chromatography (TLC) or high performance liquid chromatography (HPLC).

The fungus *Coniochaeta ellipsoidea* Udagawa, DSM 13856, can form the coniosulfides by means of a surface culture or standing culture on solid nutrient media. Solid nutrient media are prepared by adding, for example, agar or gelatin to aqueous nutrient media. However it is also possible to obtain the coniosulfides by fermenting the fungus *Coniochaeta ellipsoidea* Udagawa in the submerged method, i.e. in aqueous suspension. The coniosulfides can be present both in the mycelium and in the culture filtrate; the major quantity is normally present in the cell mass. It is therefore expedient to separate the fermentation solution by filtration or centrifugation. The filtrate is extracted using an adsorption resin as the solid phase. The mycelium, and also the surface culture, is extracted with a solvent which is miscible with water, for example with acetonitrile, n-propanol or iso-propanol, preferably with methanol or acetone, or with a solvent which is not miscible with water, for example with chloroform, dichoromethane or, preferably, with tert-butanol or ethyl acetate. Compounds of the formula (I) are preferably extracted with methanol or 2-propanol. While all the extractions can be carried out over a wide pH range, it is expedient to carry them out in neutral or weakly acid medium, preferably between pH 3 and pH 8. The extracts can be concentrated and dried in vacuo.

A method for isolating the coniosulfides according to the invention is solution partition between solvents and/or absorption partition on solids of different polarity, in a manner known per se.

Another method of purification is chromatography on adsorption resins, for example on Diaion® HP-20 (Mitsubishi Casei Corp., Tokyo), on Amberlite® XAD 7 (Rohm and Haas, USA), on Amberchrom® CG, (Toso Haas, Philadelphia, USA) or on similar resins. In addition, numerous reverse-phase supports, for example $RP_8$ and $RP_{18}$, as have become well known, for example within the context of high pressure liquid chromatography (HPLC), are suitable.

Another possibility of purifying the coniosulfide according to the invention is that of using what are termed normal-phase chromatography supports, such as silica gel or $Al_2O_3$, in a manner known per se.

An alternative isolation method is that of using molecular sieves, such as, Fractogel® TSK HW-40, Sephadex® G-25, and others, in a manner known pre se. In addition to this, it is also possible to obtain the coniosulfides by crystallizing them from enriched material. Organic solvents and their mixtures, which are free of water or which contain added water, are, for example, suitable for this purpose. An additional method for isolating and purifying the compounds according to the invention is that of using anion exchangers, preferably in the pH range of from 4 to 10, and cation exchangers, preferably in the pH range of from 2 to 5. The use of buffer solutions to which proportions of organic solvents have been added is particularly suitable for this purpose.

In addition to this, the strain *Coniochaeta ellipsoidea* Udagawa, DSM 13856, produces a tetramic acid derivative of the formula (VI),

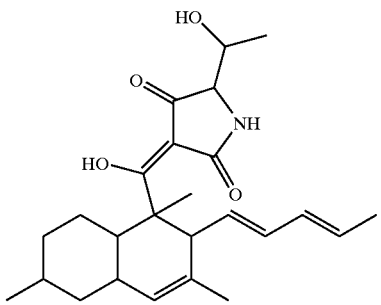
(VI)

which is termed coniosetin and which likewise inhibits the APP-FE65 reaction.

Unless otherwise indicated, chiral centers in the compound of the formula (VI) can be present in the R configuration or in the S configuration, as optically pure compounds or as stereoisomeric mixtures, such as enantiomeric mixtures and diastereomeric mixtures.

The compounds of the formula (VI) preferably possess the stereochemistry indicated in the formula (VIA):

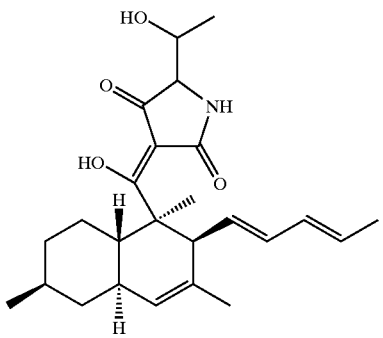
(VI A)

In order to obtain coniosetin of the formula (VI), *Coniochaeta ellipsoidea* Udagawa, DSM 13856, is fermented, with the fermentation temperature, the pH and the constituents of the culture medium corresponding to the values specified for obtaining coniosulfide and coniosulfide derivatives, with this being followed by extraction and isolation, with the extraction and purification methods corresponding to the methods specified for coniosulfide and coniosulfide derivatives. Coniosetin of formula (VI) can then optionally be converted into an obvious chemical equivalent and/or pharmacologically tolerated salt.

Obvious chemical equivalents and pharmacologically tolerated salts of compounds of the formulae (VI) and (VI A) are defined as for compounds of the formulae (I) to (V).

Coniosetin and coniosetin derivatives, a method for preparing them by fermenting *Coniochaeta ellipsoidea* Udagawa, DSM 13856, and the use of coniosetin and coniosetin derivatives as pharmaceuticals, are described in German Patent Application number DE 10060810.8.

It has been found that the compounds of the formulae (I), (II), (III), (IV), (V), (VI), and (VI A) according to the invention display strong inhibition of the amyloid precursor protein—FE65 interaction; they are therefore suitable for the treatment and prophylaxis of degenerative neuropathies and of Alzheimer's disease. Selected inhibitory constants are compiled, by way of example, in Table 1.

TABLE 1

Inhibition of the amyloid precursor protein - FE65 interaction by coniosulfide A–D and coniosetin:

| | |
|---|---|
| Coniosulfide A (formula (III)) | $IC_{50} = 2.3\ \mu M$ |
| Coniosulfide B (formula (IV)) | $IC_{50} = 2.6\ \mu M$ |
| Coniosulfide C (formula (V)) | $IC_{50} = 3.8\ \mu M$ |
| Coniosulfide D (formula (VI)) | $IC_{50} = 3.8\ \mu M$ |
| Coniosetin | $IC_{50} = 28\ \mu M$ |

The present invention consequently also relates to a pharmaceutical having a content of at least one compound of the formula (I), preferably of a compound of the formulae (II) to (V), and one or more physiologically suitable excipients and/or auxiliary substances.

The present invention furthermore relates to the use of a compound of the formula (I), preferably of a compound of the formulae (II) to (V), as a pharmaceutical.

The invention additionally relates to the use of a compound of the formula (I), preferably a compound of the formulae (II) to (V), for producing pharmaceuticals for the treatment and/or prophylaxis of the degenerative neuropathies, preferably of senile dementia or Alzheimer's disease.

The invention also relates to the use of a compound of the formula (VI), preferably of the formula (VI A), for producing pharmaceuticals for the treatment and/or prophylaxis of degenerative neuropathies, preferably of senile dementia or Alzheimer's disease.

Said pharmaceutical is produced by mixing at least one compound of the formula (I) or formula (VI) with at least one physiologically suitable excipient and/or auxiliary substance and bringing it into a suitable form for administration.

The pharmaceuticals according to the invention can be used enterally (orally), parenterally (intramuscularly or intravenously), rectally or locally (topically). They can be administered in the form of solutions, powders, tablets, capsules including microscapsules, ointments, creams, gels or suppositories. Physiologically suitable excipients or auxiliary substances for formulations of this nature are the pharmaceutically customary liquid or solid fillers and extenders, solvents, emulsifiers, glycols, taste corrigents, dyes and/or buffering substances. An expedient dose to be administered is 0.1–1000, preferably 0.2–100, mg/kg of body weight. The pharmaceuticals are expediently administered in dosage units which, for example, contain the effected daily quantity of the compounds according to the invention, e.g. 30–3000, preferably 50–1000 mg.

The following examples are intended to explain the invention in more detail, without there being any desire to restrict the breadth of the invention in any way.

EXAMPLE 1

Preparing a Glycerol Culture of *Coniochaeta ellipsoidea*, DSM 13856

30 mL of nutrient solution (malt extract, 2.0%, yeast extract, 0.2%, glucose, 1.0%, $(NH_4)_2HPO_4$ 0.05%, pH 6.0) are inoculated, in a sterile 100 mL Erlenmeyer flask, with the strain *Coniochaeta ellipsoidea* Udagawa, DSM 13856, and incubated, at 25° C. and 140 rpm, for 6 days on a rotary shaker. 1.5 ml of this culture are then diluted with 2.5 ml of 80% glycerol and stored at −135° C.

EXAMPLE 2

Preparing a Preculture of *Coniochaeta ellipsoidea* Udagawa, DSM 13856, in an Erlenmeyer Flask 100 mL of nutrient solution (malt extract, 2.0%, yeast extract, 0.2%, glucose, 1.0%, $(NH_4)_2HPO_4$ 0.05%, pH 6.0) are inoculated, in a sterile 300 mL Erlenmeyer flask, with the strain *Coniochaeta ellipsoidea* Udagawa, DSM 13856, and incubated, at 25° C. and 140 rpm, for 4 days on a rotary shaker. 2 ml of this preculture are then inoculated before preparing the main cultures.

EXAMPLE 3

Preparing a Main Culture of *Coniochaeta ellipsoidea* Udagawa, DSM 13856, on Solid Medium Plates 100 sterile 22×22 $cm^2$ plates are poured, in each case using 200 ml of the following nutrient solution: 20 g of malt extract/L, 20 g of rolled oats/L, 2% agar and pH 7.0. These plates are inoculated with 2 ml of a preculture and incubated at 25° C. The maximum production of one or more compounds of the coniosulfide according to the invention is reached after approx. 676 hours.

EXAMPLE 4

Isolating the Coniosulfides 100 of the agar cultures of *Coniochaeta ellipsoidea* Udagawa, DSM 13856, which were obtained as described in Example 3, were freeze dried. They yielded 499 g of culture lyophilisate. The lyophilisate was extracted three times with in each case 20 liters of methanol, concentrated in vacuo at room temperature and subsequently freeze-dried under high vacuum. This resulted in 79.8 g of crude extract. The lyophilized crude extract was dissolved in 25% methanol in 0.050 mol of ammonium acetate/L and pumped through a column (50×300 mm) which was filled with 0.5 liter of MCI Gel CHP20P (Mitsubishi Chemical Industries, Tokyo, Japan). The column was firstly washed with 1 L of 25 vol % acetonitrile in 75 vol % 50 mM aqueous ammonium acetate buffer and then eluted with a linear gradient of 44 vol % to 100 vol % acetonitrile in 50 mM ammonium acetate. Following HPLC-DAD analysis, the coniosulfide-containing fraction was concentrated on a rotary evaporator, in vacuo and at a bath temperature of 38° C., and freeze-dried. The yield of lyophilized coniosulfide mixture was 0.26 g. This coniosulfide mixture was dissolved in methanol and loaded onto a preparative HPLC column filled with LiChrospher RP-18e (10 $\mu m$, E. Merck, Darmstadt, Germany) (column dimensions: 25×250 $mm^2$+precolumn 25×10 $mm^2$). The RP column was firstly eluted with 30 vol % acetonitrile in 50 mM ammonium acetate buffer, at a flow rate of 50 ml per min, and then, from fraction 14 onwards, eluted with a linear gradient of from 30 vol % to 100 vol % acetonitrile in 50 mM ammonium acetate buffer. The fractions (in each case 25 ml) were analyzed in the HPLC-DAD system. Fraction 30 contained the coniosulfide A, while fraction 33 contained the coniosulfide B, fraction 28 the coniosulfide C and fraction 31 the consiosulfide D.

EXAMPLE 5

Final Purification of Coniosulfide A

The enriched coniosulfide A (fraction 30), which was obtained as described in Example 4, was fractionated on a LiChrospher® 100 RP-18e HPLC column (5 μm, width× height=1 cm×25 cm) using 50% acetonitrile in 10 mM acetic acid. Flow rate: 10 mL/min. The fractions, which were investigated by means of analytical HPLC (see Example 10), were pooled, in accordance with their coniosulfide A content, concentrated in vacuo and freeze-dried. They yield 8 mg of coniosulfide A at 98% purity.

EXAMPLE 6

Characterizing the Coniosulfide A

The physico chemical properties, and the spectroscopic properties, of coniosulfide A can be summarized as follows:
Appearance:
Colorless to pale-yellow substance which is soluble in medium-polar and polar organic solvents and not particularly soluble in water. Stable in neutral and mildly acidic medium, but unstable in strongly acid and strongly alkaline solutions.

| | |
|---|---|
| Empirical formula: | $C_{22}H_{34}O_4N_2S$; |
| Molecular weight: | 422.59 Da; |
| $^1H$ NMR and $^{13}C$-NMR: | see Table 2; |
| UV maximum: | 288 nm |

Mass-spectrometric investigations:
Coniosulfide A was assigned the mass of 422 on the basis of the following findings: $ESI^+$ spectrum yielded peaks at 423 amu $(M+H)^+$, 445 $(M+Na)^+$ and 461 $(M+K)^+$. Using a FTICR (Fourier transform ion cyclotron resonance) mass spectrometer, a peak was observed, inter alia, at 423.2314 amu. The measured value corresponds to the mass which was calculated for $(M+H)^+=C_{22}H_{35}O_4N_2S=423.2312$. MS/MS experiments using an FTICR mass spectrometer led to the following fragmentations: $ESI^+$ mode: 423 amu $(M+H)^+$ to 324 amu ($—C_4H_5NO_2$), 280 amu ($—C_5H_5NO_4$), 237 amu ($—C_7H_{10}N_2O_4$), 219 amu ($—C_{15}H_{24}$), 205 amu ($—C_7H_{10}N_2O_4S$), 100 amu ($C_4H_6O_2N+$), and smaller fragments.

TABLE 2

Chemical shifts of coniosulfide A in DMSO at 300K.

| Position | $^1H$ | $^{13}C$ |
|---|---|---|
| 1 | 1.63 | 25.44 |
| 2 | — | 130.58 |
| 2-Me | 1.55 | 17.51 |
| 3 | 5.06 | 124.08 |
| 4 | 2.02 | 26.14 |
| 5 | 1.93 | 38.98 |
| 6 | — | 134.66 |
| 6-Me | 1.56 | 15.75 |
| 7 | 5.08 | 123.52 |
| 8 | 2.06 | 25.96 |
| 9 | 2.01 | 39.0 (broad) |
| 10 | — | 139.78 |
| 10-Me | 1.68 | 15.88 |
| 11 | 5.25 | 119.57 |
| 12 | 3.50 | 30.55 |
| 13 | 7.38 | 137.6 (broad) |
| 14 | — | 122.4 (broad) |
| 15 | — | 163.69 |
| 16 | 8.99 | — |
| 17 | — | 167.28 |

TABLE 2-continued

Chemical shifts of coniosulfide A in DMSO at 300K.

| Position | $^1H$ | $^{13}C$ |
|---|---|---|
| 18 | 3.78 | 41.51 |
| 19 | 8.07 | — |
| 20 | — | 169.36 |
| 21 | 1.85 | 22.39 |

EXAMPLE 7

Final Purification and Characterization of Coniosulfide B

The enriched coniosulfide B (fraction 33), which was obtained as described in Example 4, was fractionated on a LiChrospher® 100 RP-18e HPLC column (5 μm, width× height=1 cm×25 cm) using 50% acetonitrile in 10 mM acetic acid. Flow rate: 10 mL/min. The fractions which were investigated by analytical HPLC (see Example 10), were pooled in accordance with their coniosulfide B content, concentrated in vacuo and freeze-dried. They yield 6 mg of coniosulfide B at 97% purity. The physico chemical properties and spectroscopic properties of coniosulfide B can be summarized as follows:
Appearance:
Colorless to pale-yellow substance which is soluble in medium-polar and polar organic solvents but not particularly soluble in water. Stable in neutral and mildly acidic medium but unstable in strongly acid and strongly alkaline solutions.

| | |
|---|---|
| Empirical formula: | $C_{23}H_{36}O_4N_2S$; |
| Molecular weight: | 436.62 Da; |
| $^1H$ NMR and $^{13}C$-NMR: | see Table 3; |
| UV maximum: | 288 nm |

Mass-spectrometric investigations:
Coniosulfide B was assigned the mass of 436 on the basis of the following findings: $ESI^+$ spectrum yielded peaks at 437 amu $(M+H)^+$, 459 amu $(M+Na)^+$ and 475 amu $(M+K)^+$.
High resolution of the quasi-molecule ion: using an FTICR mass spectrometer, a peak is observed, inter alia, at 437.2472 amu in the $ESI^+$ mode. The measured value corresponds to the mass calculated for $(M+H)^+=C_{23}H_{37}O_4N_2S=437.2469$.
MS/MS experiments using an FTICR mass spectrometer lead to the following fragmentations:
$ESI^+$ mode: 437 amu to 338 amu ($—C_4H_5NO_2$), 321 amu ($—C_4H_8N_2O_2$), 294 ($—C_5H_5NO_4$), 251 amu ($—C_7H_{10}N_2O_4$), 219.04 amu ($—C_{16}H_{26}$), 219.21 ($—C_7H_{10}N_2O_4S$), 100 amu ($C_4H_6O_2N+$), and smaller fragments.

TABLE 3

Chemical shifts of coniosulfide B in DMSO at 300K.

| Position | $^1H$ | $^{13}C$ |
|---|---|---|
| 1 | 1.59 | 19.83.[a] |
| 2 | — | 123.29 |
| 2-Me | 1.58 | 20.37.[a] |
| 3 | — | 135.07 |
| 3-Me | 1.58 | 18.20 |

TABLE 3-continued

Chemical shifts of coniosulfide B in DMSO at 300K.

| Position | $^1$H | $^{13}$C |
|---|---|---|
| 4 | 2.04 | 33.05 |
| 5 | 1.94 | 37.69 |
| 6 | — | 127.12 |
| 6-Me | 1.58 | 15.84 |
| 7 | 5.08 | 123.35 |
| 8 | 2.04 | 26.01 |
| 9 | 2.01 | 38.96 |
| 10 | — | 139.82 |
| 10-Me | 1.68 | 15.88 |
| 11 | 5.25 | 119.53 |
| 12 | 3.50 | 30.55 |
| 13 | 7.37 | 137.6 (broad) |
| 14 | — | 122.4 (broad) |
| 15 | — | 163.70 |
| 16 | 8.99 | — |
| 17 | — | 167.29 |
| 18 | 3.78 | 41.52 |
| 19 | 8.07 | — |
| 20 | — | 169.36 |
| 21 | 1.85 | 22.39 | a) It was not possible to assign the two methyl groups unambiguously.

EXAMPLE 8

Final Purification and Characterization of Coniosulfide C

The enriched coniosulfide C (fraction 28), which was obtained as described in Example 4, was fractionated on a LiChrospher® 100 RP-18e HPLC column (5 µm, width×height=1 cm×25 cm) using 50% acetonitrile in 10 mM acetic acid. Flow rate: 10 ml/min. The fractions, which were investigated by analytical HPLC (see Example 10), were pooled in accordance with their coniosulfide C content, concentrated in vacuo and freeze-dried. They yield 18 mg of coniosulfide C at 98% purity.

The physico chemical properties and spectroscopic properties of coniosulfide C can be summarized as follows:

Appearance:

Colorless to pale-yellow substance which is soluble in medium-polar and polar organic solvents but not particularly soluble in water. Stable in neutral and mildly acidic medium, but unstable in strongly acid and strongly alkaline solutions.

| | |
|---|---|
| Empirical formula: | $C_{24}H_{37}O_5N_3S$; |
| Molecular weight: | 479.64 Da; |
| $^1$H NMR and $^{13}$C NMR: | see Table 4; |
| UV maximum: | 288 nm |

Mass-spectrometric investigations:

Coniosulfide C was assigned the mass of 479 amu on the basis of the following findings: ESI$^+$ spectrum yielded peaks at 502 amu (M+Na)$^+$ and 518 amu (M+K)$^+$. ESI$^-$ spectrum yielded a peak at 478 amu (M–H)$^-$, inter alia.

Using an FTICR spectrometer, a peak was observed at 478.23810 amu, inter alia, in the ESI$^-$ mode. The measured value corresponds to the mass calculated for (M–H)$^-$ = $C_{24}H_{36}O_5N_3S$=478.23812 amu. MS/MS experiments using an FTICR mass spectrometer led to the following fragmentations: ESI$^-$ mode: 478 amu (M–H)$^-$ to 434 amu (—$CO_2$), 416 amu (—$H_2CO_3$) 230 amu (—$C_{15}H_{24\ c}O_2$), 229 amu (—$C_{15}H_{25}CO_2$), 196 amu ($C_8H_{10}N_3O_3{}^-$), 155 amu ($C_6H_7N_2O_3{}^-$), 154 amu ($C_6H_6N_2O_3{}^-$) and smaller fragments.

TABLE 4

Chemical shifts of coniosulfide C in DMSO at 300K.

| Position | $^1$H | $^{13}$C |
|---|---|---|
| 1 | 1.63 | 25.44 |
| 2 | — | 130.58 |
| 2-Me | 1.55 | 17.51 |
| 3 | 5.06 | 124.08 |
| 4 | 2.02 | 26.14 |
| 5 | 1.93 | 39.2 (broad) |
| 6 | — | 134.67 |
| 6-Me | 1.56 | 15.75 |
| 7 | 5.09 | 123.53 |
| 8 | 2.05 | 25.97 |
| 9 | 2.01 | 38.99 |
| 10 | — | 139.84 |
| 10-Me | 1.68 | 15.89 |
| 11 | 5.26 | 119.55 |
| 12 | 3.50 | 30.54 |
| 13 | 7.39 | 137.9 (broad) |
| 14 | — | 122.3 (broad) |
| 15 | — | 163.65 |
| 16 | 8.98 | — |
| 17 | — | 167.04 |
| 18 | 3.81 | 41.47 |
| 19 | 8.07 | — |
| 20 | — | 169.20 |
| 21 | 3.70 | 42.00 |
| 22 | 8.10 | — |
| 23 | — | 169.57 |
| 24 | 1.85 | 22.43 |

EXAMPLE 9

Final Purification and Characterization of Coniosulfide D

The enriched coniosulfide D (fraction 31), which was obtained as described in Example 4, was fractionated on a LiChrospher® 100 RP-18e HPLC column (5 µm, width×height=1 cm×25 cm) using 35% acetonitrile in 10 mM ammonium acetate buffer. Flow rate: 5 mL/min. The fractions, which were investigated by analytical HPLC (see Example 10), were pooled in accordance with their coniosulfide D content, concentrated in vacuo and freeze-dried. They yield 18 mg of coniosulfide D at 97% purity.

The physico chemical properties and spectroscopic properties of coniosulfide D can be summarized as follows:

Appearance:

Colorless to pale-yellow substance which is soluble in medium-polar and polar organic solvents but not particularly soluble in water. Stable in neutral and mildly acidic medium, but unstable in strongly acid and strongly alkaline solutions.

| | |
|---|---|
| Empirical formula: | $C_{25}H_{39}O_5N_3S$; |
| Molecular weight: | 493.67 Da; |
| $^1$H NMR and $^{13}$C-NMR: | see Table 5; |
| UV maximum: | 288 nm |

Mass-spectrometric investigations:

Coniosulfide D was assigned the mass of 493 on the basis of the following findings: ESI$^+$ spectrum yielded peaks at 494 amu (M+H)$^+$ and 516 amu (M+Na)$^+$. ESI$^-$ spectrum yields a peak at 492 amu (M–H)$^-$, inter alia.

Using an FTICR mass spectrometer, a peak was observed, inter alia, at 494.2687 amu. The measured value corresponded to that calculated for $(M+H)^+=C_{25}H_{40}O_5N_3S=$ 494.2683 amu (0.7 ppm deviation).

MS/MS experiments using an FTICR mass spectrometer lead to the following fragmentations:

ESI$^+$ mode: 494 $(M+H)^+$ to 476 ($-H_2O$), 395 ($-C_4H_5NO_2$), 338 ($-C_6H_8N_2O_3$), 294 ($-C_7H_8N_2O_6$), 157 ($-C_{19}H_{31}NO_2S$).

ESI$^-$ mode: 492 to 448 ($-CO_2$), 430 ($-CH_2O_3$), 230 ($-C_{16}H_{26}CO_2$), 229 ($-C_{16}H_{27}CO_2$), 196 ($C_8H_{10}N_3O_3^-$), 155 ($C_6H_7N_2O_3^-$), 154 ($C_6H_6N_2O_3^-$).

TABLE 5

Chemical shifts of coniosulfide D in DMSO at 300K.

| Position | $^1H$ | $^{13}C$ |
|---|---|---|
| 1 | 1.60 | 19.83.[a] |
| 2 | — | 123.28 |
| 2-Me | 1.58 | 20.36.[a] |
| 3 | — | 134.98 |
| 3-Me | 1.58 | 18.20 |
| 4 | 2.04 | 33.04 |
| 5 | 1.94 | 37.70 |
| 6 | — | 127.12 |
| 6-Me | 1.58 | 15.84 |
| 7 | 5.09 | 123.47 |
| 8 | 2.04 | 26.06 |
| 9 | 1.99 | 39.03 |
| 10 | — | 138.73 |
| 10-Me | 1.65 | 15.88 |
| 11 | 5.23 | 120.07 |
| 12 | 3.32 | 31.04 |
| 13 | 6.86 | 125.6 (broad) |
| 14 | — | —.[b] |
| 15 | — | 164.8 (broad) |
| 16 | 8.8 (broad) | — |
| 17 | — | 165.5 (broad) |
| 18 | 3.77 | 42.0 (broad) |
| 19 | 8.18 | — |
| 20 | — | 169.22 |
| 21 | 3.71 | 42.00 |
| 22 | 8.17 | — |
| 23 | — | 169.53 |
| 24 | 1.85 | 22.42 |

[a]It was not possible to assign the two methyl groups unambiguously.
[b]No signal was observed for C14 (extreme line broadening).

EXAMPLE 10

High Pressure Liquid Chromatography (HPLC) of Coniosulfide A–D

| Column: | Superspher 100 RP-18e ®, 250-4, with precolumn, |
| Mobile Phase: | 55% acetonitrile in 0.1% phosphoric acid, |
| Flow rate: | 1 mL per minute, |

Detection by UV absorption at 210 nm.

The following retention times were found:

| Coniosulfide A | 14.8 minutes; |
| Coniosulfide B | 20.1 minutes; |
| Coniosulfide C | 10.6 minutes; |
| Coniosulfide D | 14.2 minutes; |

EXAMPLE 11

Preparing a Main Culture of *Coniochaeta ellipsoidea* Udagawa, DSM 13856, on Solid Medium Plates 30 sterile 22×22 cm plates are poured using 200 ml of a nutrient solution containing 20 g of malt extract/l, 20 g of rolled oats/l and 2% agar, and having a pH of 7.0. These plates are inoculated with 2 ml of a preculture of *Coniochaeta ellipsoidea* Udagawa, DSM 13856, obtained as described in Example 2, and incubated at 25° C. The maximum production of one or more compounds of the coniosetin according to the invention is reached after approx. 676 hours.

EXAMPLE 12

Isolating Coniosetin 30 agar plates, which are each 25×25 cm in size and which are obtained as described in Example 11, are freeze-dried and extracted with 2.5 liters of methanol. The clear liquid phase is concentrated down in vacuo to 100 ml, diluted with water and loaded onto a column which has a capacity of 580 ml and is filled with the absorption resin MCI Gel® CHP20P. Column dimensions: width×height: 5 cm×30 cm. The column is eluted with a solvent gradient of from 5% acetonitrile in water to 90% acetonitrile and the column eluate (40 ml/minute) is collected in fractions of in each case 120 ml in volume. The coniosetin-containing fractions, which are checked by HPLC analyses, are collected and concentrated in vacuo and freeze-dried (0.3 g).

EXAMPLE 13

High Pressure Liquid Chromatography (HPLC) of the Coniosetin

| Column: | Superspher 100 RP-18e ®, 250-4, with precolumn, |
| Mobile Phase: | 75% acetonitrile in 0.1% phosphoric acid, |
| Flow rate: | 1 mL per minute, |

Detection by UV absorption at 210 nm.

The retention time of coniosetin is 13.6 minutes.

EXAMPLE 14

Final Purification of the Coniosetin

The enriched antibiotic coniosetin (0.3 g), obtained as described in Example 12, is fractionated on a LiChrospher® 100 RP-18e HPLC column (width×height: 2.5 cm×25 cm) by the gradient method using 75% to 100% acetonitrile in 0.05% acetic acid. Flow rate: 30 ml/min. Fraction size: 60 ml. The fractions which are investigated by HPLC (see Example 5) are pooled in accordance with their coniosetin content, concentrated in vacuo and freeze-dried. They yield 170 mg of coniosetin and 98% purity.

EXAMPLE 15

Characterizing the Coniosetin

Determining the molar peak:

The mass of 413 is assigned to the sought-after molecule on the basis of the following findings: ESI$^+$ spectrum and FAB$^+$ spectra exhibit peaks at 414 amu (M+H)$^+$. ESI$^-$ spectrum exhibits a peak at 412 amu ((M−H)$^-$, inter alia.

High resolution of the quasi-molecule ion:

Under FAB conditions, using a nitrobenzyl alcohol matrix, a peak is observed at 414.2645 amu, inter alia. The mass accuracy which exists in the measurement is approx. 5 ppm. The measured value corresponds well with the elemental composition calculated for $C_{25}H_{36}NO_4$=414.2644 amu. In this elemental composition, 9 double bond equivalents are present.

The physicochemical and spectroscopic properties of the antibiotic according to the invention can be summarized as follows:

Coniosetin:

Appearance:

Cololess to pale-yellow substance which is soluble in medium-polar and polar organic solvents but not particularly soluble in water. Stable in neutral and mildly acidic medium, but unstable in strongly acid and strongly alkaline solutions.

| Empirical formula: | $C_{25}H_{35}NO_4$ |
|---|---|
| Molecular weight: | 413.56 |
| $^1$H NMR and $^{13}$C-NMR: | see Tables 6 and 7 |
| UV maxima: | 233 nm, 288 nm |

TABLE 6

$^1$H and $^{13}$C chemical shifts of coniosetin in DMSO-d$_6$ and methanol-d$_4$ at 300K.

| | DMSO-d$_6$ | | Methanol-d$_4$ | |
|---|---|---|---|---|
| Position | $^{13}$C δ (ppm) | $^1$H δ (ppm) | $^{13}$C δ (ppm) | $^1$H δ (ppm) |
| 1 | 48.94 | — | 51.18 | — |
| 1-Me | 13.34 | 1.33 s | 14.31 | 1.42 s, br |
| 2 | 48.45 | 3.19 | 50.59 | 3.28 br |
| 3 | 130.99 | — | 133.15 | — |
| 3-Me | 22.04 | 1.53 t | 22.67 | 1.58 t |
| 4 | 125.88 | 5.19 s, br | 127.31 | 5.20 s |
| 5 | 38.61 | 1.80 | 40.68 | 1.86 m |
| 6 | 42.06 | 1.78, 0.82 | 44.10 | 1.83 d, br, 0.87 m |
| 7 | 32.90 | 1.49 | 35.00 | 1.52 m, br |
| 7-Me | 22.40 | 0.89 d | 23.07 | 0.94 d |
| 8 | 35.44 | 1.72, 1.01 | 37.20 | 1.77 d, br, 1.10 m |
| 9 | 27.59 | 1.94 d, 1.00 | 29.47 | 2.01 d, br, 1.06 m |
| 10 | 39.28 | 1.57 | 41.39 | 1.66 m |
| 11 | 130.42 | 5.18 m | 132.05 | 5.19 |
| 12 | 131.96 | 5.72 t | 134.03 | 5.78 t |
| 13 | 131.31 | 5.91 t | 132.71 | 5.90 t |
| 13a | 127.83 | 5.52 m | 129.12 | 5.51 m |
| 13b | 17.73 | 1.65 d | 18.23 | 1.67 d |
| 14 | 198.23 | — | 201.30 | — |
| 14-OH | — | 17.49 s, br | — | — |
| 15 | 99.46 | — | 101.50 | — |
| 16 | 179.52 | — | 181.53 | — |
| 17 | — | 9.22 s, br | — | — |
| 18 | 66.57 | 3.62 | 68.19 | 3.62 br |
| 19 | 191.09 | — | 193.51 | — |
| 20 | 65.66 | 3.91 | 68.11 | 4.06 br |
| 20-OH | — | 4.76 d | — | — |
| 21 | 20.67 | 1.17 d | 20.65 | 1.29 d, br |

TABLE 7

$^1$H and $^{13}$C chemical shifts of coniosetin in CDCl$_3$ at 300K.

| Position | $^{13}$C δ (ppm) | $^1$H δ (ppm) |
|---|---|---|
| 1 | 49.84 | — |
| 1-Me | 13.76 | 1.44 |
| 2 | 49.25 | 3.22 |
| 3 | 131.50 | — |
| 3-Me | 22.23 | 1.61 |
| 4 | 126.01 | 5.20 |
| 5 | 39.13 | 1.85 |
| 6 | 42.54 | 1.82, 0.90 |
| 7 | 33.54 | 1.54 |
| 7-Me | 22.46 | 0.94 |
| 8 | 35.78 | 1.79, 1.13 |
| 9 | 28.30 | 1.99, 1.08 |
| 10 | 39.73 | 1.68 |
| 11 | 130.19 | 5.23 |
| 12 | 132.62 | 5.83 |
| 13 | 131.39 | 5.89 |
| 13a | 128.19 | 5.52 |
| 13b | 18.02 | 1.70 |
| 14 | 200.23 | — |
| 14-OH | — | — |
| 15 | 100.28 | — |
| 16 | 179.33 | — |
| 17 | — | 6.19 |
| 18 | 65.43 | 3.71 |
| 19 | 190.95 | — |
| 20 | 67.80 | 4.05 |
| 20-OH | — | — |
| 21 | 19.56 | 1.34 |

EXAMPLE 16

Test for the Ability to Inhibit the APP-FE65 Interaction

| HEPES, | Sigma, H-9136, |
|---|---|
| NaCl, | Riedel de Haen, 31434, |
| EDTA, | Sigma, E-1644, |
| CHAPS, | Sigma, C-5849, |
| KF, | Sigma, P-1179, |
| BSA, | Sigma, A-9647 |
| Monoclonal anti-GST antibody labeled with XL665, | CIS bio Intern., D11/459/12/47270; |
| Streptavidin labeled with Eu-cryptate, | CIS bio Intern., D11/450/12/47269; |
| 32mer cAPP, | Sigma, E2533; |
| Biotin-cAPP, | Aventis SA, Vitry. |

Buffer A:
10 mM HEPES, pH 7.2+150 mM NaCl+3.4 mM EDTA+ 0.184 g of CHAPS/L.
Buffer B:
100 mM HEPES, pH 7.0+400 mM KF+133 mM EDTA+1 g BSA/L.
Implementation:
1 μl of the solution to be tested was pipetted, together with 30 μM 32 mer cAPP in Buffer A, into a microtiter plate. 1 μl of biotin-cAPP (10 nM, dissolved in Buffer A) was then added. After incubating for 15 minutes, 1 μL of GST-PTB2 (20 nM in Buffer A) was added and the plate was incubated once again for 15 minutes. 4 μl of antibody mixture (Streptavidin labeled with Eu-cryptate, 2 mg per well; monoclonal anti-GST antibody labeled with XL665, 25 mg in Buffer B) were then added. After 30 minutes at room temperature, the emission signal of the energy transfer, and the europium signal, were measured at 665 nm and 615 nm in a Tecan ultraphotometer after the test solution had been activated with light at a wavelength of 340 nm.

The IC50 values listed in Table 1 were found for the inhibition of the amyloid precursor protein—FE65 interaction.

What is claimed is:

1. A compound of formula (I)

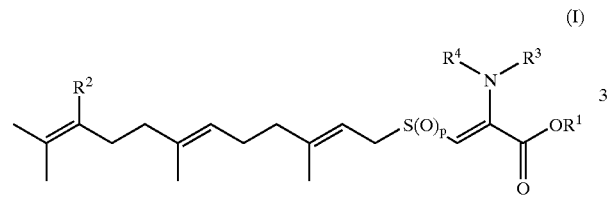

(I)

where
R$^1$ is
(a) H, or
(b) a radical selected from —C$_1$–C$_6$-alkyl, —C$_2$–C$_6$-alkenyl, —C$_2$–C$_6$-alkynyl or —C$_6$–C$_{10}$-aryl, which is substituted once or twice by
(b1) —OH,
(b2) =O,
(b3) —O—(C$_1$–C$_6$-alkyl),
(b4) —O—(C$_2$–C$_6$-alkenyl),
(b5) —C$_6$–C$_{10}$-aryl,
(b6) —NH—C$_1$–C$_6$-alkyl,
(b7) —NH—C$_2$–C$_6$-alkenyl,
(b8) —NH$_2$ or
(b9) fluorine, chlorine, bromine or iodine, in which the substituents (b3) to (b8) is optionally substituted by —CN, -amide or -oxime functions, or
(c) —(C$_1$–C$_4$-alkyl)–(C$_6$–C$_{10}$-aryl), or
(d) —NH$_2$, —NH—(C$_1$–C$_6$-alkyl), or —NH—(C$_2$–C$_6$-alkenyl),
R$^2$ is H, methyl, ethyl, n-propyl, isopropyl, n-butyl or iso-butyl,
R$^3$ is a radical which is composed of from 1 to 10 amino acids and which is optionally N-terminally protected,
R$^4$ is H, —C$_1$–C6-alkyl, or —CO—(C$_1$–C$_6$-alkyl), and
p is an integer 0, 1 or 2,
with the exception of the compounds of the formula (I) in which, at the same time,
R$^1$ is H,
R$^2$ is H,
R$^3$ is —CO—CH$_3$,
R$^4$ is H, and
p is 0 or 1,
and/or a stereoisomeric form of the compound of the formula (I) and/or mixtures of this form in any ratio,
and/or a physiologically tolerated salt of the compound of the formula (I).

2. A compound of the formula (I) as claimed in claim 1, where
R$^4$ is H, and
R$^1$, R$^2$, R$^3$ and p are defined as in claim 1.

3. A compound of the formula (I) as claimed in claim 1, where
R$^4$ is H, and
p is 0, and
R$^1$, R$^2$ and R$^3$ are defined as in claim 1.

4. A compound of the formula (I) as claimed in claim 1, where
R$^2$ is H or methyl,
R$^4$ is H,
p is 0, and
R$^1$ and R$^3$ are defined as in claim 1.

5. A compound of the formula (I) as claimed in claim 1, where
R$^2$ is H or methyl,
R$^3$ is a radical which is composed of from 1 to 2 amino acids and which can be N-terminally protected,
R$^4$ is H,
p is 0, and
R$^1$ is defined as in claim 1.

6. A compound of the formula (I) as claimed in claim 1, where
R$^1$ is H,
R$^2$ is H or methyl,
R$^3$ is a radical which is composed of from 1 to 2 amino acids and which can be N-terminally protected,
R$^4$ is H, and
p is 0.

7. A compound of the formula (II)

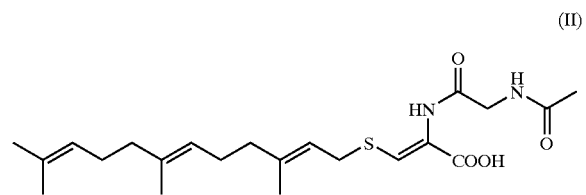

(II)

and the physiologically tolerated salts thereof.

8. A compound of formula (III):

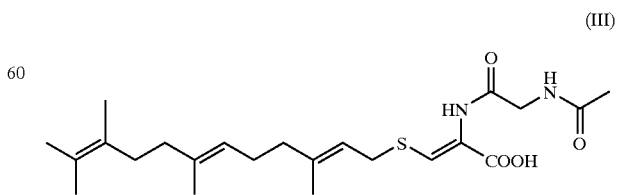

(III)

and the physiologically tolerated salts thereof.

9. A compound of formula (IV)

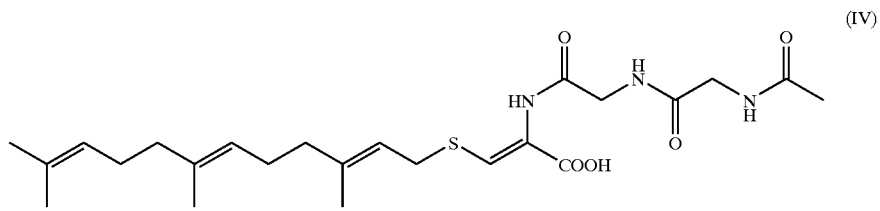

and the physiologically tolerated salts thereof.

10. A compound of formula (V)

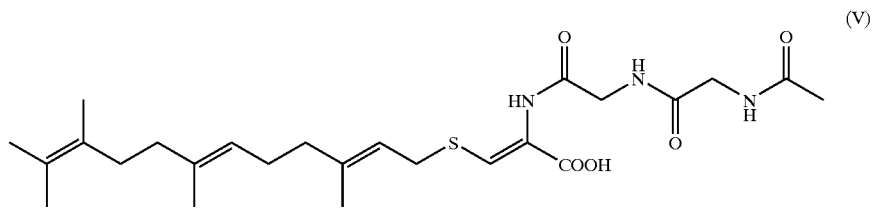

and the physiologically tolerated salts thereof.

11. A process for preparing a compound of formula (I), which comprises fermenting the microorganism *Coniochaeta ellipsoidea* Udagawa, DSM 13856, or a variant or mutant of *Coniochaeta ellipsoidea* Udagawa, DSM 13856, in a culture medium until a compound of the formula (I) accumulates in the culture medium, isolating the compound of the formula (I) and then optionally derivatizing it and, where appropriate, converting it into a physiologically tolerated salt.

12. A pharmaceutical comprising at least one compound as claimed in claim 1 and at least one physiologically suitable excipient and/or auxiliary substance.

13. A pharmaceutical comprising at least one compound as claimed in claim 7 and at least one physiologically suitable excipient.

14. A pharmaceutical comprising at least one compound as claimed in claim 8 and at least one physiologically suitable excipient.

15. A pharmaceutical comprising at least one compound as claimed in claim 9 and at least one physiologically suitable excipient.

16. A pharmaceutical comprising at least one compound as claimed in claim 10 and at least one physiologically suitable excipient.

* * * * *